United States Patent [19]
Prencipe et al.

[11] Patent Number: 6,106,812
[45] Date of Patent: *Aug. 22, 2000

[54] DUAL COMPONENT ANTIPLAQUE AND TOOTH WHITENING COMPOSITION

[75] Inventors: Michael Prencipe, Princeton Junction; Mike Wong, North Brunswick; Vincent O. Drago, Sayreville; Marcus Bentley, Jersey City; Mahmoud Hassan, Piscataway; Nagaraj S. Dixit, Plainsboro, all of N.J.

[73] Assignee: Colgate-Palmolive Company

[ * ] Notice: This patent is subject to a terminal disclaimer.

[21] Appl. No.: 09/231,042

[22] Filed: Jan. 13, 1999

Related U.S. Application Data

[63] Continuation-in-part of application No. 09/166,025, Oct. 5, 1998.

[51] Int. Cl.[7] .............................. A61K 7/16; A61K 7/18; A61K 7/20
[52] U.S. Cl. ................................................ 424/53
[58] Field of Search ......................... 424/49–58

[56] References Cited

U.S. PATENT DOCUMENTS

| | | | |
|---|---|---|---|
| 5,055,209 | 10/1991 | Bridges et al. | 252/8.51 |
| 5,122,365 | 6/1992 | Murayama | 424/53 |
| 5,256,402 | 10/1993 | Prencipe et al. | 424/53 |
| 5,279,816 | 1/1994 | Church et al. | 424/53 |
| 5,302,375 | 4/1994 | Viscio | 424/53 |
| 5,372,802 | 12/1994 | Barrows et al. | 424/53 |
| 5,401,495 | 3/1995 | Murayama | 424/53 |
| 5,424,060 | 6/1995 | Hauschild | 424/53 |
| 5,571,501 | 11/1996 | Toy | 424/49 |
| 5,578,293 | 11/1996 | Prencipe et al. | 424/49 |
| 5,601,803 | 2/1997 | Masters et al. | 424/49 |
| 5,614,174 | 3/1997 | Hsu et al. | 424/49 |
| 5,616,313 | 4/1997 | Williams et al. | 424/53 |
| 5,632,972 | 5/1997 | Williams et al. | 424/53 |
| 5,648,064 | 7/1997 | Gaffar et al. | 424/53 |
| 5,683,680 | 11/1997 | Santalucia et al. | 424/53 |
| 5,690,911 | 11/1997 | Mirajkar et al. | 424/49 |
| 5,690,913 | 11/1997 | Hsu et al. | 424/53 |
| 5,693,314 | 12/1997 | Campbell et al. | 424/49 |
| 5,698,182 | 12/1997 | Prencipe et al. | 424/53 |
| 5,718,886 | 2/1998 | Pellico | 424/53 |
| 5,730,959 | 3/1998 | Prencipe et al. | 424/53 |
| 5,756,073 | 5/1998 | Miller et al. | 424/49 |
| 5,766,574 | 6/1998 | Christina-Beck et al. | 424/53 |
| 5,776,437 | 7/1998 | Burgess et al. | 424/53 |
| 5,785,956 | 7/1998 | Sullivan et al. | 424/52 |
| 5,800,803 | 9/1998 | Mirajkar et al. | 424/49 |
| 5,820,852 | 10/1998 | Burgess et al. | 424/53 |
| 5,820,853 | 10/1998 | Glandorf | 424/52 |
| 5,820,854 | 10/1998 | Glandorf | 424/53 |
| 5,843,406 | 12/1998 | Mordarski et al. | 424/49 |
| 5,846,570 | 12/1998 | Barrow et al. | 424/53 |
| 5,849,269 | 12/1998 | Burgess et al. | 424/53 |
| 5,853,704 | 12/1998 | Zhang et al. | 424/52 |
| 5,885,553 | 3/1999 | Michael | 424/53 |
| 5,885,555 | 3/1999 | Sheehan | 424/53 |
| 5,939,052 | 8/1999 | White et al. | 424/52 |

*Primary Examiner*—Shep K. Rose
*Attorney, Agent, or Firm*—Paul Shapiro

[57] ABSTRACT

A dual component tooth whitening composition is disclosed, which composition contains a peroxide whitening and a second ingredient incompatible with the peroxide compound, the second ingredient and the peroxide compound each being incorporated in separate dentifrice components which are physically separated until dispensed for use, the components retaining their original physical state when in contact, the first component being a composition containing a peroxide whitening compound in a vehicle thickened with a combination of a particulated water insoluble inorganic compound and an organic thickener other than an alkylene oxide polymer, and the second component containing the ingredient incompatible with the peroxide.

24 Claims, No Drawings

DUAL COMPONENT ANTIPLAQUE AND TOOTH WHITENING COMPOSITION

This application is a continuation-in-part of copending patent application U.S. Ser. No. 09/166,025 filed Oct. 5, 1998.

BACKGROUND OF THE INVENTION

1. Field of the Invention

The present invention relates to a dual component oral care composition which is stable and efficacious in effecting heightened whitening of teeth.

2. The Prior Art

Many substances such as tea and coffee that a person confronts or comes in contact with on a daily basis can "stain" or reduce the "whiteness" of one's teeth. Consumers consider clean, white teeth to be aesthetically desirable. Dull-looking, stained teeth are objectionable to most people both on the basis of cosmetic appearance and also socially as an indication of poor oral hygiene.

Dental gels containing active oxygen liberating ingredients such as hydrogen peroxide, urea peroxide, percarbonates and perborates of alkali and alkaline earth metals have been disclosed in the prior art for whitening teeth. For example, U.S. Pat. No. 5,766,574 discloses a dual component dental whitening composition which comprises packaging a first gel component containing a peroxide compound and a second paste component containing silica present in amounts which is incompatible with the peroxide, the first and second dentifrice components being maintained separate from the other in a dual chambered container or tube until dispensed and combined for application to teeth requiring whitening.

It has been further determined that many dentifrice thickening or gelling agents are incompatible with hydrogen peroxide. Organic thickeners such as polyoxyethylene oxide/polypropylene oxide block copolymers although compatible with hydrogen peroxide, the block copolymer structure completely collapses when the dentifrice component containing the polymer comes in contact even for a short time, as in U.S. Pat. No. 5,766,574 with a dentifrice containing an incompatible ingredient, whereby the gel is converted to an unacceptable liquid state. This phenomenon is especially troublesome when small amounts of paste and gel residue mix at the tip of the dual chambered dentifrice dispenser, which results in a liquid forming that dribbles down the dispenser surface which is unappealing to the consumer. When the two components are packaged in a dual chambered tube wherein there is a pinhole, or tear in the dividing membrane, liquefaction of the gel occurs, especially during storage at elevated temperatures, e.g., 120° F.

Although the composition disclosed in U.S. Pat. No. 5,766,574 is effective for whitening, when a noncationic antiplaque agent such as Triclosan is included in the abrasive dentifrice component, it was discovered that when the peroxide gel and paste components were combined for application to the teeth, the bioavailability of the Triclosan was inhibited to a level whereby a limited antiplaque benefit was achieved. Investigation of this problem led to the discovery that polyethylene oxide/polypropylene oxide block copolymers conventionally used as a thickening agents in the preparation of peroxide gels were the factor responsible for the impairment of the antiplaque efficacy of the Triclosan. A solution to this problem is disclosed in copending application U.S. Ser. No. 09/166,025 which is directed to a dental product capable of delivering both an antiplaque agent such as Triclosan and a peroxide whitening agent whereby the ingredients used to prepare the dentifrice composition do not inhibit the bioavailability of the antiplaque agent so that optimum antiplaque and whitening benefits result, wherein the antibacterial agent and/or peroxide compound are each incorporated in separate dentifrice components which are physically separated until dispensed for use, the first component being an aqueous composition containing the nonionic antibacterial agent and the second component containing a peroxide whitening compound in a vehicle thickened with a combination of a inorganic thickener and an organic thickener other than an alkylene oxide polymer, whereby unimpaired antiplaque, and whitening benefits are achieved upon mixing of the components on application to the teeth.

It has now been determined that the combination of thickener ingredients used in the peroxide gels of U.S. Ser. No. 09/166,025 also impart storage stability to the gel so that the gel does not liquefy when in contact with the paste component.

SUMMARY OF THE INVENTION

In accordance with the present invention, there is provided a composition and method for applying a dental composition containing a peroxide whitening compound and a second ingredient incompatible with the peroxide compound wherein the second ingredient and the peroxide compound are each incorporated in separate dentifrice components which are physically separated until dispensed for use which components retain their original physical state when in contact, the first component being a composition containing a peroxide whitening compound in a vehicle thickened with a combination of a particulated water insoluble inorganic compound and an organic thickener other than an alkylene oxide polymer, such as a polyethylene oxide/polypropylene oxide block copolymer, and the second component contains the ingredient incompatible with the peroxide.

DESCRIPTION OF THE PREFERRED EMBODIMENTS

In the practice of the present invention, the peroxide whitening component is formulated as a gel using a vehicle containing the peroxide whitening compound in a water/humectant vehicle containing a thickening combination of a particulated water insoluble inorganic compound and an organic thickening compound other than an alkylene oxide polymer.

Examples of suitable peroxide compounds used to prepare the whitening component of the present invention include metal ion free peroxide ingredients such as hydrogen peroxide and organic peroxides such as urea peroxide, glyceryl peroxide and benzoyl peroxide as well as metal ion containing peroxides such as calcium peroxide, and sodium percarbonate. A preferred peroxide compound is hydrogen peroxide.

Typically, the peroxide compound is employed in the composition of the present invention in amounts so that at least about 0.1% by weight of the whitening component comprises a peroxide. Preferably, the peroxide compound comprises from about 1 to about 3% by weight of the whitening component.

Glycerin and polyethylene glycol in combination with water are useful in formulating the vehicle for the peroxide gel whitening component of the present invention. Glycerin and polyethylene glycol are included in the peroxide gel component of the present invention in an amount of from about 2 to about 80% by weight and preferably about 10 to about 50% by weight. Water is incorporated in the gel component of the present invention at a concentration of about 5 to about 90% by weight of the composition and preferably about 15 to about 50% by weight.

The thickening agent used for the formulation of the peroxide gel whitening component is a combination of a particulated water insoluble inorganic compound and an organic thickener other than an alkylene oxide polymer. The thickening agent combination is present in the peroxide gel component in an amount within the range of about 0.1 to about 10% by weight and preferably about 3 to 10% by weight.

Examples of particulated water insoluble inorganic compounds useful in the preparation of the thickening combination include inorganic thickeners such as fumed silicas such as those available from Cabot & Degussa Corporation under the trademark Cab-o-Sil and Aerosil, clays such as Laponite available from Southern Clay Company and amorphous silicas available from the Huber Company under the trademark Zeodent 115, alumina and mica. The particulated water insoluble inorganic compounds may be incorporated in the peroxide gel at a concentration of from about 0.05% to about 2% by weight, and preferably from about 0. 1% to about 1% by weight.

Examples of organic thickeners which may be used in the preparation of the peroxide gel component in combination with the inorganic thickener include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, hydroxyethyl cellulose, and carboxyvinyl polymers and partially neutralized carboxyvinyl polymers. Carboxyvinyl polymers are commercially available under the trademarks "Carbopol 934, 940, 974 P" from B.F. Goodrich and Synthalen K available from 3V Company, such polymers consisting of water soluble polymers of polyacrylic acid cross-linked with from about 0.75% to about 2% of polyallyl sucrose or polyallyl pentaerythritol as a crosslinking agent, often with molecular weights of 4 to 5 million or more. The organic thickener may be incorporated in the peroxide gel component of the present invention at a concentration of about 0.1 to about 5% by weight and preferably about 1.0 to about 3.0% by weight.

The peroxide gel component may be prepared by suspending the peroxide in a vehicle thickened with a combination of inorganic and organic thickeners by mixing in any suitable mixing device.

It is critical to the practice of the present invention that a combination of particulated water insoluble inorganic compounds such as inorganic thickeners and organic thickeners be used in the preparation of the peroxide gel component. If organic thickeners alone are used in the formulation of the peroxide gel, the rheology of the gel does not resemble that of a dentifrice and lacks the stand-up properties usually associated with dentifrices. If inorganic thickeners alone are used, such as fumed silica, the gel tends to stiffen considerably on aging, resulting in a peroxide gel component that will have a rheology which is in a state of flux and will not be extruded from a dual chamber package in amounts of equal proportion to the paste product. If a clay such as Laponite alone is used, the product will not be stable to peroxide ingredients.

The second component in which an ingredient incompatible with peroxide is included is generally a paste prepared using a vehicle which contains water, humectant, abrasive, surfactant and thickener ingredients.

The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 80% by weight and preferably about 40 to about 50% by weight. The water content is in the range of about 10 to about 80% by weight, and preferably from 20% to 50%.

Thickeners which may be used in the preparation of the second paste component include thickening silicas, such as amorphous silica available from J.M. Huber Company under the trademark Zeodent 115, natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The thickener may be incorporated in the paste component of the present invention at a concentration of about 0.1 to about 3% by weight and preferably about 0.5 to about 1% by weight.

Surfactants are incorporated in the paste component to provide foaming properties. The surfactant is preferably anionic. Suitable examples of anionic surfactants include higher alkyl sulfates such as potassium or sodium lauryl sulfate which is preferred, higher fatty acid monoglyceride monosulfates, such as the salt of the monosulfated monoglyceride or hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine. The surfactant is generally present in the antiplaque paste component at a concentration of about 0.5 to about 5.0% by weight of the component.

Incompatible ingredients included in the second paste component include nonionic antibacterial agents, abrasives and antitartar agents.

Nonionic antibacterial agents used in the preparation of the second, paste component include halogenated diphenyl ether compounds such as 2,4,4'-trichloro-2'-hydroxydiphenyl ether (triclosan) and 2,2'-dihydroxy-5,5'-dibromodihenyl ether. Other useful nonionic antibacterial agents include phenoic compounds including phenol and its homologs, mono and polyalkyl and aromatic halopehnols, resorcinol and its derivatives and bisphenolic compounds, such phenolic compounds being more fully disclosed in U.S. Pat. No. 5,368,844, the disclosure of which is incorporated herein by reference. The antibacterial agent is incorporated in the paste component of the composition of the present invention at a concentration of about 0.5 to about 3.0% by weight and preferably about 0.1 to about 1% by weight.

Abrasives which may be incorporated in the paste component include siliceous materials, such as silica and alumina. A preferred silica is a precipitated amorphous hydrated silica, such as Sorbosil AC-35, marketed by Crossfield Chemicals, or Zeodent 115 from Huber Company. Alumina abrasives include alumina trihydrate, aluminum silicate, calcined alumina and bentonite. The concentration of abrasive in the paste component of the present invention will normally be in the range of 10 to about 50% by weight and preferably 20 to 40% by weight.

Antitartar agents effective against dental calculus used in the preparation of the second dentifrice component include pyrophosphate salts such as the mono, di, tri, and tetraalkali metal and ammonium pyrophosphate and tripolyphosphate salts. Such agents are used in amounts sufficient to reduce calculus and are preferably in amounts which will release at least about 1.0% by weight $P_2P_7$ ion and include such salts as sodium tripolyphosphate and tetrasodium and tetra potassium pyrophosphate, the salts being present in the second dentifrice components in amounts from about 2% to 10% by weight and preferably about 2 to about 7% by weight.

Fluoride ion-providing salts having anti-caries efficacy may also be incorporated in the paste component of the present invention and are characterized by their ability to release fluoride ions in water and include sodium fluoride, potassium fluoride, a tin fluoride such as stannous fluoride, sodium fluorosilicate, ammonium fluorosilicate and sodium monofluorophosphate. It is preferable to employ a fluoride salt to release about 10–1500 ppm of fluoride ion.

Synthetic anionic polycarboxylates may optionally be included in the second paste component. Anionic polycarboxylates are well known, being often employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to 1,000,000. These copolymers are available for example as Gantrez AN 139 (M.W. 500,000), AN 119 (M.W. 250,000) and preferably S-97 Pharmaceutical Grade of GAF Corporation. Other operative polymeric polycarboxylates include those disclosed in U.S. Pat. No. 3,956,480, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates include those disclosed in U.S. Pat. No. 4,138,477, and U.S. Pat. No. 4,183,914, such as copolymers of maleic anhydride with styrene, isobutylene or ethyl vinyl ether, polyacrylic, polyitaconic and polymaleic acids, and sulfoacrylic oligomers of molecular weight as low as 1,000, available as Uniroyal ND-2.

Plaque buffers such as calcium lactate, calcium glycerophosphate and stronthium polyacrylates may also be included in the abrasive component. Other optional ingredients include vitamins such as vitamin A, C, E, $B_6$, $B_{12}$, K, plant extracts as well as potassium salts useful in the treatment of dentin hypersensitivity such as potassium citrate, potassium chloride, potassium sulfate, potassium tartrate and potassium nitrate.

Peroxide activators such as manganese coordination complexes such as manganese gluconate may also be incorporated in the antiplaque paste component of the present invention. The activator compound when contacted with the peroxide ingredient of the peroxide gel component activates the peroxide compound and accelerates the release of active oxygen to effect rapid whitening action. Other examples of manganese coordination complexes useful for incorporation in the second dentifrice component as peroxide activators are described in U.S. Pat. No. 5,648,064 which is incorporated herein by reference. The manganese coordination complex compounds are included in the second dentifrice component at a concentration of about 0.005% to about 3% by weight and preferably about 0.05 to about 1.75% by weight.

Other ingredients which may be incorporated in the dentifrice components of the present invention include pigments, dyes, flavoring and sweetening materials. A striped dental product is obtained in accordance with the practice of the present invention wherein colorants of contrasting colors are incorporated in each of the components used in the practice of the present invention, the colorants being pharmacologically and physiologically nontoxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentifrice component and are generally food color additives presently certified under the Food Drug & Cosmetic Act for use in food and ingested drugs, including dyes such as FD&C Red #3 (sodium salt of tetraiodofluorescein), FD&C Yellow #5 (sodium salt of 4-p-sulfophenylaxo-B-naphtol-6-monosulfonate), FD&C Green #3 (disodium salt of 4-{[4-(N-ethyl-p-sulfobenzylamino)-phenyl]-4-hydroxy-2-sulfoniumphenyl)-methylene}-[1-(N-ethyl-N-p-sulfobenzyl)-3,5-cyclohexadienimine], FD&C Blue #1 (disodium salt of dibenzyldiethyl-diaminotriphenylcarbinol trisulfonic acid anhydrite), FD&C Blue #2 (sodium salt of disulfonic acid of indigotin) and mixtures thereof in various proportions. The concentration of the dye for the most effective result in the present invention is present in an amount from about 0.0005% to about 2% by weight.

It is preferred that the colorant included in one of the components be a pigment such as $TiO_2$ and that the colorant distributed throughout the body of the other component be a dye and that the dye be of a different color than the colorant included in the first dentifrice component.

Any suitable flavoring or sweetening material may also be incorporated in the components of the present invention. Examples of suitable flavoring constituents are flavoring oils, e.g., oils of spearmint, peppermint, wintergreen, sassafras, clove, sage, eucalyptus, marjoram, cinnamon. Lemon, and orange, and methyl salicylate. Suitable sweetening agents include sucrose, lactose, maltose, sorbitol, xylitol, sodium cyclamate, perillartine, and sodium saccharin. Suitably, flavor and sweetening agents may together comprise from 0.01% to 5% by weight or more of the preparations.

To prepare the paste component of the present invention, water, humectant, e.g., sorbitol, thickener and sweetener are dispersed in a conventional mixer until the mixture becomes a homogeneous gel phase. Into the gel phase are added a pigment such as $TiO_2$ and a fluoride anticaries agent such as sodium fluoride. These ingredients are mixed until a homogeneous phase is obtained. Thereafter the abrasive, polycarboxylate compound, antibacterial agent, tartar control ingredients, peroxide activator, flavor and surfactant ingredients are added and the ingredients mixed at high speed under vacuum of about 20–100 mm Hg. The resultant product is a homogeneous, semi-solid, extrudable paste product.

The dual component oral composition of the present invention is packaged in a suitable dispensing container in which the components are maintained physically separated and from which the separated components may be dispensed synchronously. Such containers are known to the art. An example of such container is a dual compartmented dispensing container having collapsible sidewalls disclosed in U.S.

Pat. Nos. 4,487,757 and 4,687,663 wherein the container body is formed from a collapsible plastic web and is provided with a partition within the container body defining separate compartment in which the physically separated components are stored and from which they are dispersed through a suitable dispensing outlet.

The following Examples illustrate the present invention. The individual components described below were prepared by following the procedures described above. The amounts of the various ingredients are by weight unless otherwise indicated.

EXAMPLE I

Toothpaste components designated Paste A-1 and A-2 were prepared containing ingredients (abrasive silica, tetrasodium pyrophosphate, sodium tripolyphosphate and Triclosan) which were incompatible with peroxide compounds, the composition of these pastes, in weight % is recorded in Table I below. A series of gels of the present invention containing both an organic and inorganic thickeners designated Gels B, D, E were also prepared, as well as a comparative gel, designated, Gel C which did not contain a particulated water insoluble inorganic compound. The compositions of these gels in weight % are also listed in Table I below.

EXAMPLE II

A series of peroxide gels thickened with Carbopol were prepared and the viscosity of the gels using a Caramed Rheometer were measured and are recorded in Table II.

TABLE II

| | Gel Component (Weight %) | | |
|---|---|---|---|
| Ingredients | F | G | H |
| Glycerin | 40.0 | 38.0 | 40.0 |
| Xanthan | 0.4 | 0.4 | 0.4 |
| Carbopol | 2.0 | 1.75 | 2.0 |
| $H_2O_2$ | 5.71 | 5.71 | 5.71 |
| PEg 600 | 10.0 | 10.0 | 10.0 |
| Fumed silica | — | 0.10 | — |
| Laponite | 0.1 | — | — |
| FD & C Blue #1 (1% sol.) | 0.7 | 0.70 | 0.70 |
| Water | QS to 100 | QS to 100 | QS to 100 |
| pH | 4.7 | 4.6 | 4.7 |
| Viscosity Pa · S | 96 | 101 | 16 |

*Viscosity measured at 5 sec$^{-1}$ at 25° C. using a Carrimed Rheometer equipped with 4 centimeter parallel plates.

Reference to Table II indicates that Gel H prepared with the organic thickeners, Carbopol and xanthan and without any inorganic thickener had very little structure as indicated

TABLE I

| | Dentifrice Component (Weight %) | | | | | |
|---|---|---|---|---|---|---|
| Ingredients | Paste A-1 | Paste A-2 | Gel B | Gel C | Gel D | Gel E |
| Glycerin | 12.00 | 20.00 | 40.00 | 30.00 | 38.00 | 29.75 |
| Carboxymethyl cellulose | 0.55 | 0.8 | — | — | — | — |
| Carbopol 974P | — | — | 2.0 | — | 1.75 | 2.0 |
| Carrageenan | 0.24 | 0.3 | — | — | — | — |
| Xanthan | — | — | 0.40 | — | 0.5 | 0.4 |
| Pluronic F-127 | — | — | — | 21.0 | — | — |
| Hydrogen Peroxide(35% sol.) | — | — | 5.71 | 5.71 | 5.71 | 5.71 |
| NaF | 0.243 | 0.243 | 0.243 | 0.243 | 0.243 | 0.243 |
| Mn Gluconate | 0.05 | 0.50 | — | — | — | — |
| Saccharin | 0.45 | 0.30 | 0.25 | 0.1 | 0.1 | 0.25 |
| Sorbitol | 22.6 | 9.00 | — | — | — | — |
| Polyethylene glycol | — | — | 10.0 | 10.0 | 10.0 | 10.0 |
| Gantrez Liquid | 7.69 | 30.00 | — | — | — | — |
| NaOH (50%) | 2.00 | 2.40 | — | — | — | — |
| Abrasive Silica | 31.00 | 20.0 | — | — | — | 0.2 |
| Silica Thickener | — | 1.0 | — | — | — | — |
| Fumed Silica | — | — | — | — | 0.1 | — |
| Laponite | — | — | 0.10 | — | — | — |
| Flavor | 1.9 | 1.90 | 0.3 | 0.3 | 0.3 | 0.3 |
| Triclosan | — | 0.60 | — | — | — | — |
| SLS | 2.0 | 2.50 | — | — | — | — |
| Tetrasodium pyrophosphate | 1.00 | — | 0.10 | — | — | — |
| Sodium tripolyphosphate | 7.00 | — | — | — | — | — |
| FD & C Blue #1 (1% solution) | — | — | 1.05 | 0.70 | 1.05 | 1.05 |
| Phosphoric acid | — | — | — | 1.0 | — | — |
| $TiO_2$ | 1.00 | 0.50 | — | — | — | — |
| Water | QS 100% | QS | QS | QS | QS | QS |

A two compartment tube was filled with Paste A-1 in one compartment and the other with Gel B. Before filling, pinholes were formed with a needle in the divider which separated the tubes into compartments. For purposes of comparison, the tube filling procedure was repeated except Gel C was substituted for Gel B. After storage at 120° F. For 3 weeks, Gel C had liquefied whereas as Gel B was still in its original semi-solid extrudible state.

by the low viscosity as measured at 5 sec.-1. However, when small amounts of inorganic thickeners were included in the composition, such as 0.1% by weight Laponite (Dentifrice Component F) or 0.1% fumed silica (Dentifrice Component G), the viscosity was enhanced dramatically, Gels F and G exhibiting acceptable stand up and reduced stringiness.

EXAMPLE III

Bovine teeth stained with tea and coffee were soaked with 1:1 compositions of the Paste A-1 and Gel B of Table I, the combined components being designated Composition X.

The % stain removed as a function of time is recorded in Table III below. For purposes of comparison the procedure of Example III was repeated except a commercially available abrasive dentifrice containing 24% by weight silica was as used as a control and the amount of stain removed during the soaking exposure was also recorded in Table III below.

TABLE III

| Product | Soaking Time (hrs.) | % Stain Removed |
| --- | --- | --- |
| Commercial silica abrasive dentifrice | 6 | 6.5 |
|  | 24 | 6.3 |
| Composition X | 6 | 95.3 |
|  | 24 | 100.0 |

The results recorded in Table III indicate that after 6 hours, 95% of the stain is removed from the teeth by soaking in Composition X indicating that Gel B did not interfere with the whitening efficacy of H2O2. By comparison, the commercial dentifrice did not remove any significant amount of stain even after 24 hours of soaking.

EXAMPLE IV

The antiplaque activity of 1:1 combined dentifrice components Paste A-2 and Gel D of Table I designated Composition Y was assessed using a saliva flow cell model of the type disclosed in the Journal of Dental Research, Vol. 73(11), pgs. 1748–1755 (1994).

In the Flow Cell System, after each experiment, approximately 5 hours after the last treatment, the flow cells were rinsed with distilled water for 15 minutes at a flow rate of 1 mL/min. Bacterial plaque formed on hydroxyapatite (HAP) disks was removed by immersing the disks in 2 mL of 0.1 mol/L NaOH in a shaking water bath at 37° C. for 45 min. After the disks were removed, the sample was sonicated for plaque dispersion. Turbidity of the resulting solution was measured at 610 nm in a spectrophotometer.

The plaque mass accumulated on the HAP disks is directly proportional to the optical density measurement: the lower the plaque mass, the lower the optical density, and the greater the antiplaque efficacy of the composition. A commercial antiplaque toothpaste containing 0.3% by weight Triclosan, designated Composition Z was used as a control. The plaque mass results are recorded in Table IV below.

TABLE IV

| Composition | Plaque Mass |
| --- | --- |
| Y | 0.12 |
| Z | 0.26 |

The results recorded in Table IV show that compared to the commercial Triclosan toothpaste Z, the antiplaque activity of Composition Y was not impaired.

TABLE V

| Ingredients | Gel J | Gel K | Gel L |
| --- | --- | --- | --- |
| Carbopol 974 | 2.0 | 2.0 | 2.0 |
| Glycerin | 27.75 | 27.75 | 27.75 |
| Water | 50.072 | 50.072 | 50.072 |
| Sodium hydroxide (50% sol.) | 0.2 | 0.2 | 0.2 |
| Polyethylene glycol 600 | 10.0 | 10.0 | 10.0 |
| Xanthan | 0.4 | 0.4 | 0.4 |
| Sodium fluoride | 0.243 | 0.243 | 0.243 |
| Sodium saccharin | 0.25 | 0.25 | 0.25 |
| Hydrogen peroxide | 5.71 | 5.71 | 5.71 |
| Flavor | 0.3 | 0.3 | 0.3 |
| Glycerin | 2 | 2 | 2 |
| Alumina | 0 | 0.2 | 0 |
| Timeron* | 0 | 0 | 0.2 |
| Blue Dye #1 (1% sol.) | 0.875 | 0.875 | 0.875 |
| Brookfield viscosity (3 wks. @ RT)** | 11.0 | 18.00 | 18.00 |

*Hydrous aluminum magnesium silicate coated on titanium dioxide.
**Brookfield viscosity no. 95T spindle @ 5 rpm.

Gels J, K and L were semi-solid compositions exhibiting acceptable stand up and reduced stringiness. Gels J, K and L were stable after aging for 3 weeks at 120° F.

What is claimed is:

1. A dual component tooth whitening composition the components of which when mixed together contain a peroxide whitening and a second ingredient incompatible with the peroxide compound, the second ingredient and the peroxide compound each being incorporated in separate dentifrice components which are physically separated until dispensed for use, the components retaining their original semi-solid physical state when in contact, the first component being a semi-solid abrasive free gel composition containing a peroxide whitening compound in a vehicle thickened with a combination of a particulated water insoluble inorganic compound and an organic thickener other than an alkylene oxide polymer, and the second component being a semi-solid paste containing the ingredient incompatible with the peroxide, the first and second components when in contact retain their semi-solid physical state.

2. The composition of claim 1 wherein the incompatible ingredient is a nonionic antibacterial agent.

3. The composition of claim 1 wherein the incompatible ingredient is sodium tripolyphosphate.

4. The composition of claim 1 wherein the incompatible ingredient is manganese gluconate.

5. The composition of claim 1 wherein the organic thickener is selected from natural and synthetic gums and polymers.

6. The composition of claim 3 wherein the organic thickener is xanthan.

7. The composition of claim 3 wherein the organic thickener is a carboxyvinyl polymer.

8. The composition of claim 1 wherein the particulated water insoluble inorganic compound is an inorganic thickener.

9. The composition of claim 8 wherein the inorganic thickener is Laponite.

10. The composition of claim 8 wherein the inorganic thickener is fumed silica.

11. The composition of claim 8 wherein the inorganic thickener is present in the peroxide component from about 0.05 to about 2% by weight.

12. The composition of claim 1 wherein the organic thickener is present in the peroxide component from about 0.1 to about 10% by weight.

13. A method for whitening treatment of teeth which comprises preparing a dual component composition in which a first component is a semi-solid abrasive paste and the second component is a semi-solid abrasive free gel composition containing a peroxide compound in a vehicle thickened with a combination of an particulated water insoluble compound and an organic thickener compound other than an alkylene oxide polymer, and the second component containing an ingredient incompatible with the peroxide compound and is free of an alkylene oxide polymer maintaining the first component physically separated from a second component, the first and second components when in contact retain their semi-solid physical state and thereafter mixing the extruded components upon application to the teeth.

14. The method of claim 13 wherein the incompatible ingredient is a nonionic antibacterial agent.

15. The method of claim 13 wherein the incompatible ingredient is sodium tripolyphosphate.

16. The composition of claim 13 wherein the incompatible ingredient is manganese gluconate.

17. The method of claim 13 wherein the organic thickener is selected from natural and synthetic gums and polymers.

18. The method of claim 13 wherein the organic thickener is xanthan.

19. The method of claim 13 wherein the organic thickener is a carboxyvinyl polymer.

20. The method of claim 13 wherein the particulated water insoluble inorganic compound is an inorganic thickener.

21. The method of claim 20 wherein the inorganic thickener is Laponite.

22. The method of claim 20 wherein the inorganic thickener is fumed silica.

23. The method of claim 13 wherein the inorganic compound is present in the peroxide component from about 0.01 to about 2% by weight.

24. The method of claim 13 wherein the organic thickener is present in the peroxide component from about 0.1 to about 10% by weight.

* * * * *